United States Patent [19]
Bright et al.

[11] Patent Number: 5,958,948
[45] Date of Patent: Sep. 28, 1999

[54] SUBSTITUTED PYRAZOLES AS CRF ANTAGONISTS

[75] Inventors: Gene M. Bright, Groton; Willard M. Welch, Jr., Mystic, both of Conn.

[73] Assignee: Pfizer, Inc., New York, N.Y.

[21] Appl. No.: 08/933,963

[22] Filed: Sep. 19, 1997

Related U.S. Application Data

[62] Division of application No. 08/481,348, Jun. 14, 1995, Pat. No. 5,705,646.

[51] Int. Cl.$^6$ ........................ C07D 401/06; A61K 31/415
[52] U.S. Cl. ......................... 514/314; 514/406; 546/152; 548/373.1; 548/375.1
[58] Field of Search ............................ 546/152; 514/314, 514/406; 548/373.1, 375.1

[56] References Cited

U.S. PATENT DOCUMENTS 4,605,642  8/1986  Rivier et al. ............................. 514/12
5,063,248  11/1991  Abren et al. ............................. 514/404

*Primary Examiner*—Zinna Northington Davis
*Attorney, Agent, or Firm*—Peter C. Richardson; Paul H. Ginsburg; B. Timothy Creagan

[57] ABSTRACT

The compounds of the formula

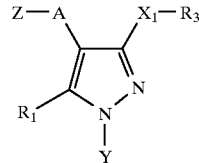

wherein A, $R_1$, $R_3$, $X_1$, Y and Z are as defined herein, have corticotropin-releasing factor (CRF) antagonist activity. They are useful in the treatment of illnesses induced by CRF, such as stress and anxiety related disorders.

4 Claims, No Drawings

SUBSTITUTED PYRAZOLES AS CRF ANTAGONISTS

This is a division, of application Ser. No. 08/481,348, filed on Jun. 14, 1995 now U.S. Pat. No. 5,705,646.

This invention relates to substituted pyrazoles, pharmaceutical compositions containing them, and their use in the treatment of stress-related and other diseases. The compounds have corticotropin-releasing factor (CRF) antagonist activity.

CRF antagonists are mentioned in U.S. Pat. Nos. 4,605,642 and 5,063,245 referring to peptides and pyrazolinones, respectively. The importance of CRF antagonists is set out in the literature, e.g. as discussed in U.S. Pat. No. 5,063,245, which is incorporated herein by reference. A recent outline of the different activities possessed by CRF antagonists is found in M. J. Owens et al., Pharm. Rev., Vol. 43, pages 425 to 473 (1991), also incorporated herein by reference. Based on the research described in these two and other references, CRF antagonists are considered effective in the treatment of a wide range of diseases including stress-related illnesses, such as stress-induced depression, anxiety, and headache; abdominal bowel syndrome; inflammatory diseases; immune suppression; human immunodeficiency virus (HIV) infections; Alzheimer's disease; gastrointestinal diseases; anorexia nervosa; hemorrhagic stress; drug and alcohol withdrawal symptoms; drug addiction, and fertility problems.

The present invention relates to a compound of the formula

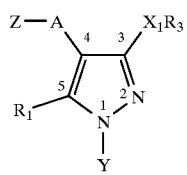

I and the pharmaceutically acceptable acid addition salts thereof, wherein

A is $CH_2$;

$R_1$ is hydrogen; linear or branched $C_1$–$C_6$ alkyl; $C_3$–$C_6$ alkyl containing one or two non-adjacent double bonds; hydroxy; $O(C_1$–$C_6$ alkyl); SH; $S(C_1$–$C_6$ alkyl); $C_3$–$C_6$ cycloalkyl; morpholinyl, piperidinyl or aryl which aryl may be substituted by one to three of fluoro, chloro, bromo, trifluoromethyl, hydroxy, $O(C_1$–$C_6$ alkyl), SH, $S(C_1$–$C_6$ alkyl), amino, $NH(C_1$–$C_6$ alkyl), $N(C_1$–$C_6$ alkyl)$_2$, or one of iodo, nitro or cyano, said aryl being selected from the group consisting of phenyl, thienyl, benzothienyl, pyridyl, quinolyl, pyrazinolyl, pyrimidyl, imidazolyl, benzimidazolyl, furanyl, benzofuranyl, thiazolyl, benzothiazolyl, isothiazolyl, benzoisothiazolyl, isoxazolyl, benzisoxazolyl, triazolyl, pyrazolyl, pyrrolyl, indolyl, azaindolyl, oxazolyl, benzoxazolyl, pyrrolidinyl, and thiazolidinyl;

$R_3$ is linear $C_1$–$C_6$ alkyl, branched $C_3$–$C_8$ alkyl, $C_3$–$C_8$ alkenyl wherein the double bond is not adjacent to $X_1$ when $X_1$ is a heteroatom, or $C_3$–$C_7$ cycloalkyl($CH_2$)$_n$ wherein n is 0 to 4, or $(CH_2)_qQ_1R_{19}$ wherein q is 0, 1 or 2, $Q_1$ is O, S, NH, $N(C_1$–$C_6$ alkyl), or a covalent bond when $X_1$ is not a covalent bond, and $R_{19}$ is hydrogen, linear $C_1$–$C_6$ alkyl, branched $C_3$–$C_8$, $C_3$–$C_8$ alkenyl, $C_3$–$C_6$ cycloalkyl or $C_3$–$C_6$ cycloalkyl ($CH_2$);

$X_1$ is a covalent bond, $CH_2$, O, S, or NR, wherein R is hydrogen or linear $C_1$–$C_6$ alkyl or branched $C_3$–$C_8$ alkyl;

Y is phenyl, thienyl, benzothienyl, pyridyl, quinolyl, pyrazinolyl, pyrimidyl, imidazolyl, benzimidazolyl, furanyl, benzofuranyl, thiazolyl, benzothiazolyl, isothiazolyl, benzisothiazolyl, isoxazolyl, benzisoxazolyl, triazolyl, pyrazolyl, pyrrolyl, indolyl, azaindolyl, oxazolyl, benzoxazolyl, pyrrolidinyl, thiazolidinyl, morpholinyl, or piperidinyl, each of which may be substituted by one to three of any one of fluoro, chloro, bromo, or methyl, or one of trifluoromethyl; with the proviso that Y is not unsubstituted phenyl; and Z is

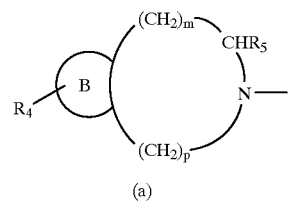

II (a)

wherein the B ring is phenyl, naphthyl, pyridyl, pyrimidinyl, pyrazinyl, pyridazinyl, triazolyl, pyrrolyl, pyrazolyl, imidazolyl, thienyl, or indolyl, each of which may be substituted by methyl, methoxy, trifluoromethyl, fluoro, chloro, bromo or iodo; or a saturated 5- or 6-membered carbocyclic ring or a partially unsaturated ring having one or two double bonds;

$R_4$ is hydrogen, $C_1$–$C_6$ alkyl, $C_1$–$C_6$ alkoxy, hydroxy, fluoro, chloro, bromo, iodo, or trifluoromethyl;

$R_5$ is hydrogen, linear $C_1$–$C_6$ alkyl, branched $C_3$–$C_8$ alkyl, $C_3$–$C_8$ alkenyl, or $(CH_2)_o$—$X_2$—$(CH_2)_r$—$Q_2$—$R_6$;

$X_2$ and $Q_2$ are each independently O, S, NH, $N(C_1$–$C_6$ alkyl), or one of $X_2$ and $Q_2$ may be a covalent bond;

$R_6$ is hydrogen, linear $C_1$–$C_6$ alkyl, branched $C_3$–$C_8$ alkyl or $C_3$–$C_8$ alkenyl;

m is 0 or 1;

o is 1 or 2;

p is 1 or 2; and r is 0, 1 or 2

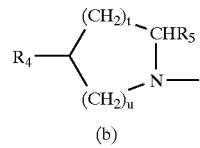

III (b)

wherein $R_4$ and $R_5$ are as defined above, and t and u are each independently 1 or 2;

(c) —$NR_7R_8$ wherein $R_7$ and $R_8$ are each independently hydrogen, $C_1$–$C_6$ linear alkyl, branched $C_3$–$C_8$ alkyl, $C_3$–$C_8$ alkenyl, $(CH_2)_vCH_2OH$, $(CH_2)_vNR_9R_{10}$, wherein v is 0 to 3, and $R_9$ and $R_{10}$ are each independently hydrogen, or linear $C_1$–$C_6$ alkyl; $(C_3$–$C_{12}$ cycloalkyl) $(CH_2)_n$, $(C_6$–$C_{10}$ bicycloalkyl) $(CH_2)_n$, benzofused $C_3$–$C_6$ cycloalkyl, $C_1$–$C_6$ hydroxyalkyl, phenyl $(CH_2)_n$, each of which may be substituted by one or two of hydroxy, fluoro, chloro, bromo, $C_1$–$C_5$ alkyl, or $C_1$–$C_5$ alkoxy; or $R_7$ and $R_8$ may be taken together with the nitrogen to form a saturated or partially unsaturated 5- to 7-membered ring which may contain one of O, S, NH or $N(C_1$–$C_6$ alkyl) and which may be substituted by $C_1$–$C_6$ alkyl, hydroxy or phenyl wherein any double bond(s) are not adjacent to any heteroatoms; and n is 0 to 4;

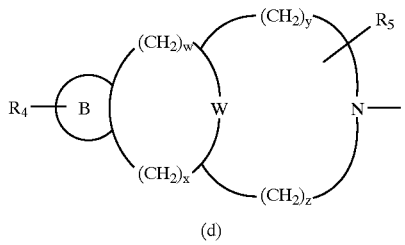

(d)

wherein B, $R_4$ and $R_5$ are as defined above, w, x, y and z are each independently 1 or 2, and W is $(CH_2)_q$ wherein q is as defined above, $N(C_1-C_6$ alkyl), or oxygen;

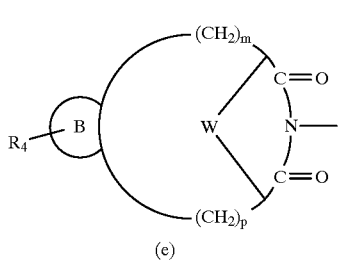

(e)

wherein B, W, $R_4$, m and p are as defined above;

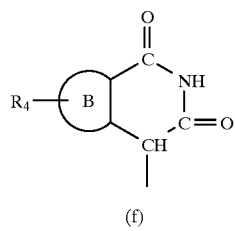

(f)

wherein B and $R_4$ are as defined above;

(g) $O(CH_2)_vR_{11}$ wherein v is 0 to 3 and $R_{11}$ is linear $C_1-C_6$ alkyl, branched $C_3-C_8$ alkyl, phenyl, naphthyl, 1,2,3,4-tetrahydronaphthyl, thienyl, benzothienyl, pyridyl, quinolyl, pyrazinolyl, pyrimidyl, imidazolyl, benzimidazolyl, furanyl, benzofuranyl, thiazolyl, benzothiazolyl, isothiazolyl, benzisothiazolyl, isoxazolyl, benzisoxazolyl, triazolyl, pyrazolyl, pyrrolyl, indolyl, azaindolyl, oxazolyl, benzoxazolyl, pyrrolidinyl, thiazolidinyl, morpholinyl, piperidinyl, or thienyl, each of which may be substituted by one or two of any one of fluoro, chloro, bromo, methyl, or trifluoromethyl;

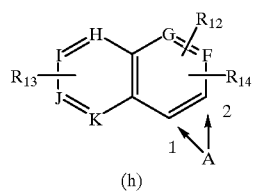

(h)

wherein A is as defined above and is linked to position 1 or 2 while $R_{14}$ is attached to position 2 or 1, respectively; F, G, H, I, J and K are independently C or N, provided that not more than three of H, I, J and K are N with not more than two adjacent nitrogens; $R_{12}$ and $R_{13}$ each independently are hydrogen, linear $C_1-C_6$ alkyl, branched $C_3-C_8$ alkyl, $C_3-C_8$ alkenyl, fluoro, chloro, bromo, trifluoromethyl, hydroxy, thiol, $C_1-C_{12}$ alkoxy, $C_1-C_{12}$ thioalkanyl, or $C_3-C_{12}$ alkenoxy or $C_3-C_{12}$ thioalkenyl wherein the double bond is not adjacent to the oxygen or sulfur; and $R_{14}$ is hydroxy, $C_1-C_{12}$ alkoxy, $C_3-C_{12}$ alkenoxy wherein the double bond is not adjacent to the oxygen, or $-X_2-(CH_2)_rQ_2R_6$ wherein $X_2$, r, $Q_2$ and $R_6$ are as defined above in paragraph (a) except that $Q_2$ is not sulfur, or $R_{14}$ is $NR_{15}R_{16}$ wherein $R_{15}$ and $R_{16}$ are each independently hydrogen, linear $C_1-C_6$ alkyl, branched $C_3-C_8$ alkyl, $C_3-C_8$ alkenyl wherein the double bond is not adjacent to the nitrogen, or $C_3-C_7$ cycloalkyl-$(CH_2)_n$ wherein n is as defined above, or $R_{15}$ and $R_{16}$ together with the nitrogen form a saturated five or six membered ring optionally condensed with benzo; or

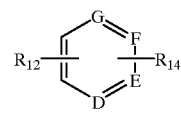

wherein D, E, F and G are independently C or N, provided that not more than two of D, E, F and G are N, $R_{12}$ and $R_{14}$ are as defined above, A, defined above, is linked to a carbon in formula VIII, and $R_{14}$ is linked to a carbon located adjacent to the carbon to which A is linked.

Preferred compounds of formula I are those wherein Z is 1,2,3,4-tetrahydroquinolin-2-yl substituted by $R_5$ which is $(CH_2)_0-X_2-(CH_2)_r-Q_2-R_6$, or more preferably $R_5$ is $(CH_2)_kOH$ wherein k is 1 to 4, or $CH_2OCH_2CH_2OR_6$. Other preferred compounds are those wherein Z is 1,2,3,4-tetrahydroisoquinolin-2-yl, wherein $R_5$ is substituted at position 3, and the absolute configuration at the 3-position is S or R or R,S. Further preferred compounds are those wherein Z is of the formula

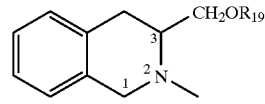

with the absolute configuration at position 3 determined by its derivation from (+)-3-hydroxymethyl-1,2,3,4-tetrahydroisoquinolin, wherein $R_{19}$ is methyl, ethyl, isopropyl, cyclopropylmethylene, or 2-hydroxyethyl, and, more preferably, wherein in addition $XR_3$ is ethyl or methylthio, Y is 2,6-dichloro-4-trifluoromethylphenyl, 2,4,6-trichlorophenyl, 2,4,6-trimethylphenyl, 2,6-dimethyl-4-bromophenyl, or 2,6-dibromo-4-fluorophenyl, and $R_1$ is methyl or ethyl.

More specific compounds of formula I are those wherein Z is as defined in (h), and, more specifically, A is linked to position 1, and $R_{14}$ is at position 2 and is $X_2-(CH_2)_rQ_2R_6$; or A is linked to position 1, F, G, H, I, J, and K are each carbon, and $R_{14}$ is 2-methoxy, 2-ethoxy, 2-isopropoxy, or 2-cyclopropylmethoxy; or A is linked to position 1, K is nitrogen, F, G, H, I and J are each carbon, and $R_{14}$ is at position 2 and is $X_2-(CH_2)_rQ_2R_6$; or A is linked to position 1, K is nitrogen, F, G, H, I, and J are each carbon, and $R_{14}$ is at position 2 and is methoxy, ethoxy, isopropoxy, or cyclopropylmethoxy, $HOCH_2CH_2O-$, or $CH_3OCH_2CH_2O$; or A is at position 1 and $R_{14}$ is at position 2 and is ethoxy, isopropoxy, cyclopropylmethoxy, $HOCH_2CH_2O$ or $CH_3OCH_2CH_2O$—.

More specific compounds of formula I include those wherein Z is

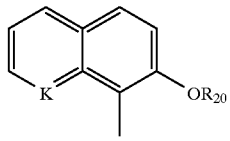

wherein K is C or N and $R_{20}$ is methyl, ethyl, isopropyl, cyclopropylmethylene, methoxyethylene, hydroxyethylene, and, more specifically, in addition $X_1R_3$ is ethyl or methylthio, Y is 2,6-dichloro-4-trifluoromethylphenyl, 2,4,6-trichlorophenyl or 2,6-dibromo-4-fluorophenyl, and $R_1$ and $R_2$ are each methyl or ethyl.

Other more specific compounds are those of formula I wherein Z is as defined in (a), B is phenyl, p and m are each 1, and $R_5$ is $CH_2OCH_3$ or $CH_2OCH_2CH_2OH$; and those wherein Z is

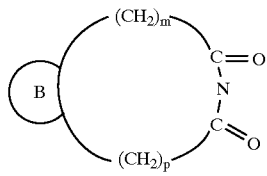

More specific compounds of formula I of the invention include those wherein Y is phenyl substituted by three substituents one each at positions 2, 4 and 6, e.g. 2,4,6-trichlorophenyl, 2,6-dimethyl-4-bromophenyl, 2,6-dichloro-4-trifluoromethylphenyl, 2,6-dichloro-4-fluorophenyl or 2,4,6-trimethylphenyl. Other more specific compounds of formula I include those wherein $X_1R_3$ is ethyl or methylthio, those wherein $R_1$ is ($C_1$–$C_6$) alkyl, and those wherein Z is $NR_7R_8$ and $R_7$ is phenyl or phenyl substituted by one of fluoro, chloro, nitro, methyl or methoxy and $R_8$ is as defined above, preferably, $(CH_2)_3OH$, $CH_2CH_2OH$ or methyl.

Specific, preferred compounds of formula I include 3-methoxymethyl-2-[5-methyl-3-methylsulfanyl-1-(2,4,6-trichlorophenyl)-1H-pyrazol-4-ylmethyl]-1,2,3,4-tetrahydroisoquinoline; (3R)-3-methoxymethyl-2-[5-methyl-3-methylsulfanyl-1-(2,4,6-trichlorophenyl)-1H-pyrazol-4-ylmethyl]-1,2,3,4-tetrahydroisoquinoline; 3-methoxymethyl-2-[5-methyl-3-methylsulfanyl-1-(2,6-dichloro-4-trifluoromethylphenyl)-1H-pyrazol-4-ylmethyl]-1,2,3,4-tetrahydroisoquinoline; {2-[5-methyl-3-methylsulfanyl-1-(2,4,6-trichlorophenyl)-1H-pyrazol-4-ylmethyl]-1,2,3,4-tetrahydroisoquinolin-3-yl}methanol; {2-[5-methyl-3-methylsulfanyl-1-(2,6-dichloro-4-trifluoromethylphenyl)-1H-pyrazol-4-ylmethyl]-1,2,3,4-tetrahydroisoquinolin-3-yl}methanol; 2-{1-(2,6-dichloro-4-trifluoromethylphenyl)-3,5-diethyl-1H-pyrazol-4-ylmethyl]-naphthalene-2-yloxy}-ethanol; 2-{8-[1-(2,6-dichloro-4-trifluoromethylphenyl)-3,5-diethyl-1H-pyrazol-4-ylmethyl]-quinolin-7-yloxy}-ethanol; 2-[3,5-diethyl-1-(2,4,6-trichlorophenyl)-1H-pyrazol-4-ylmethyl]-3-methoxymethyl-1,2,3,4-tetrahydroisoquinoline; or 1-(2,6-dichloro-4-trifluoromethylphenyl)-3,5-diethyl-4-(2-methoxynaphthalen-1-ylmethyl)-1H-pyrazole; 2-{2-[1-(2,6-dichloro-4-trifluoromethylphenyl)-3,5-diethyl-1H-pyrazol-4-ylmethyl]-1,2,3,4-tetrahydro-isoquinolin-3-ylmethoxy}-ethanol; 2-{1-[3,5-diethyl-1-(2,4,6-trimethylphenyl)-1H-pyrazol-4-ylmethyl]-naphthalen-2-yloxy}-ethanol; 2-[1-(4-bromo-2,6-dimethylphenyl)-3,5-diethyl-1H-pyrazol-4-ylmethyl]-3-methoxymethyl-1,2,3,4-tetrahydroisoquinoline; 2-[1-(4-bromo-2,6-dimethylphenyl)-3,5-diethyl-1H-pyrazol-4-ylmethyl]-3-ethoxymethyl-1,2,3,4-tetrahydroisoquinoline; and 2-{2-[3,5-diethyl-1-(2,4,6-trimethylphenyl)-1H-pyrazol-4-ylmethyl]-1,2,3,4-tetrahydro-isoquinolin-3-ylmethoxy}-ethanol.

Specific, most preferred compounds of formula I include 2-[1-(2,6-dichloro-4-trifluoromethylphenyl)-3,5-diethyl-1H-pyrazol-4-ylmethyl]-3-methoxymethyl-1,2,3,4-tetrahydroisoquinoline, 2-[3,5-diethyl-1-(2,4,6-trimethylphenyl)-1H-pyrazol-4ylmethyl]-3-ethoxymethyl-1,2,3,4-tetrahydroisoquinoline, 2-[1-(2,6-dichloro-4-trifluoromethyl-phenyl)-3,5-diethyl-1H-pyrazol-4-ylmethyl]-3-methoxymethyl-1,2,3,4-tetrahydrosioquinoline, and 2-[3,5-diethyl-1-(2,4,6-trimethylphenyl)-1H-pyrazol-4-ylmethyl]-3-ethoxymethyl-1,2,3,4-tetrahydroisoquinoline.

The invention includes a compound of the formula IA (not shown) and the pharmaceutically acceptable acid addition salt thereof. The compounds of the formula IA are identical to those of formula I except that A is $CH(C_1$–$C_6$ alkyl), $C(C_1$–$C_6$ alkyl)$_2$, $C(C_1$–$C_6$ alkyl)($C_3$–$C_8$ alkenyl)$_2$, or $CH(CH_2)_n(C_3$–$C_8$ alkenyl) wherein n is 0 to 4.

The invention also relates to a pharmaceutical composition for the treatment of (a) illnesses induced or facilitated by corticotropin releasing factor or (b) stress and anxiety related disorders, including stress-induced depression and headache, abdominal bowel syndrome, immune suppression, HIV infections, Alzheimer's disease, gastrointestinal disease, anorexia nervosa, hemorrhagic stress, drug and alcohol withdrawal symptoms, drug addiction, and fertility problems, which comprises a compound of the formula I or IA as defined above in an amount effective in the treatment of said illnesses or disorders, and a pharmaceutically acceptable carrier. Preferred compositions of the invention are those containing preferred compounds of formula I as described above.

The invention further relates to a method for the treatment of illnesses induced or facilitated by corticotropin releasing factor by administering to a subject in need of such treatment a compound of formula I or IA as defined above in an amount effective in such treatment, and a method for the treatment of stress and anxiety related disorders, including stress-induced depression and headache, abdominal bowel syndrome, inflammatory disorders, immune suppression, HIV infections, Alzheimer's disease, gastrointestinal diseases, anorexia nervosa, hemorrhagic stress, drug and alcohol withdrawal symptoms, drug addiction, and fertility problems, particularly depression, by administering to a subject in need of such treatment a compound of formula I or IA as defined above in an amount effective in such treatment. Preferred methods of the invention are those administering a preferred compound of the formula I as described above.

The invention also relates to an intermediate compound of the formula

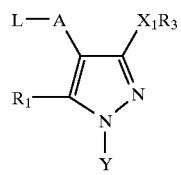

wherein A is $CH_2$, $R_3$ is linear $C_1$–$C_6$ alkyl, branched $C_3$–$C_8$ alkyl, $C_3$–$C_8$ alkenyl wherein the double bond is not adjacent to the N or $X_1$ when $X_1$ is oxygen or sulfur, $C_3$–$C_7$ cycloalkyl $(CH_2)_n$ wherein n is 0, 1, 2, 3 or 4; or $(CH_2)_q Q_1 R_6$ wherein q is 0, 1 or 2, $Q_1$ is O, S, NH, N($C_1$–$C_6$ alkyl) or a covalent bond, and $R_6$ is hydrogen, linear $C_1$–$C_6$ alkyl, branched $C_3$–$C_8$ alkyl, $C_3$–$C_8$ alkenyl, $C_3$–$C_6$ cycloalkyl, or $C_3$–$C_6$ cycloalkyl $(CH_2)_n$ wherein n is 0 to 4, with the proviso that when q is 1, then $X_1$ and $Q_1$ can not both be a heteroatom;

$X_1$ is a covalent bond, $CH_2NR$, wherein R is hydrogen or linear $C_1$–$C_6$ alkyl, O, or S;

Y is phenyl, thienyl, benzothienyl, pyridyl, quinolyl, pyrazinolyl, pyrimidyl, imidazolyl, benzimidazolyl, furanyl, benzofuranyl, thiazolyl, benzothiazolyl, isothiazolyl, benzisothiazolyl, isoxazolyl, benzisoxazolyl, triazolyl, pyrazolyl, pyrrollyl, indolyl, azaindolyl, oxazolyl, benzoxazolyl, pyrrolidinyl, thiazolidnyl, morpholinyl, or piperidinyl, each of which may be substituted by one to three of any one of fluoro, chloro, bromo, or methyl, or one of trifluoromethyl, provided that Y is not unsubstituted phenyl, and L is chloro, bromo, iodo, hydroxy, $O(C=O)(C_1$–$C_6$ alkyl), $OSO_2(C_1$–$C_6$ alkyl), $OSO_2$aryl wherein said aryl is phenyl which may be substituted by one to three of fluoro, chloro, bromo, hydroxy, $O(C_1$–$C_6$ alkyl), SH, $S(C_1$–$C_6$ alkyl), amino, $NH(C_1$–$C_6$ alkyl), $N(C_1$–$C_6$ alkyl)$_2$, or one of iodo, nitro or cyano.

Whenever reference herein is made to the groups $(CH_2)_q Q_1 R_{19}$ and $(CH_2)_0$—$X_2$—$(CH_2)_r Q_2 R_6$, then $X_1$ and $Q_1$, and $X_2$ and $Q_2$, respectively, are not both a heteroatom when q or r, respectively, is 1.

Whenever $R_1$ or Y is a heterocyclic group, the attachment of the group is through a carbon atom.

The compounds of formula I may be prepared by reaction of a compound of the formula

IX

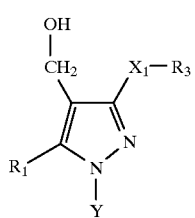

wherein $R_1$ and Y are as defined above with reference to formula I with a compound of the formula ZH wherein Z is as defined above.

This reaction generally proceeds at temperatures ranging from about 0° to 85° C., usually at room temperature. The reaction is conveniently carried out in a solvent which is inert under the reaction conditions, e.g. acetonitrile. The compound of formula IX is first reacted with an activated sulfonic acid such as methylsulfonyl chloride in the presence of an acid neutralizing agent such as triethylamine in an inert solvent such as methylene chloride at about −10° to about 50° C., before reaction with ZH.

The compounds of formula IX may be prepared by reacting a compound of the formula

X

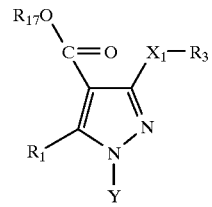

wherein $R_1$, $X_1$ and Y are as defined with reference to formula I and $R_{17}$ is $C_1$–$C_6$ alkyl, with a reducing agent such as diisobutylaluminum hydride at temperatures of about −10° to about 80° C., in a reaction-insert solvent such as tetrahydrofuran or ether.

The compounds of formula X may be prepared by reaction of a compound of the formula

XI

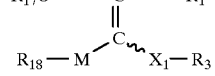

with a compound of the formula Y—$NHNH_2$, wherein $X_1$, $R_1$, $R_3$ and Y are as defined with reference to formula I, M is O or S, $R_{17}$ is as defined above with reference to formula X, and $R_{18}$ is $C_1$–$C_6$ alkyl. The reaction is usually carried out in a solvent, such as a $C_1$–$C_8$ alcohol, at least 50 to 150° C., conveniently the reflux temperature of the reaction mixture. The wavy line ～ in formula XI indicates that either isomer of this compound is included, in accordance with accepted conventions for indicating stereoisomers.

The compounds of formula XI above may be prepared by reacting an appropriate beta-ketoester with a base such as sodium hydride in the presence of carbon disulfide in an appropriate solvent or mixture of solvents such as dimethylsulfoxide or dimethylformamide at a temperature of about −10° to about 40° C. followed by quenching of the resulting dianion with an appropriate alkylating agent such as methyl iodide resulting in a 3,3-bismethylthioacrylate derivative XI wherein $R_{18}$ is $R_3$ is $CH_3$ and M is $X_1$ is S. Reaction of compounds of the formula XI wherein M is $X_1$ is S and $R_3$ is $R_{18}$ is $C_1$–$C_6$ alkyl with alcohols $R_3OH$ in the presence of base then results in the preparation of the corresponding compounds XI wherein $R_{18}$ is $R_3$ and M is $X_1$ is O.

Reaction of an appropriate beta-ketoester with an ortho ester of one of the following formulas:

($C_1$–$C_6$ alkyl)-$(CH_2)_n$—C[O—($C_1$–$C_6$ alkyl)]$_3$;
($C_2$–$C_8$ alkenyl)-$(CH_2)_n$—C[O—($C_1$–$C_6$ alkyl)]$_3$; or
$R_{19}Q_1(CH_2)_q$—$X_1$—$(CH_2)_n$—C[O—($C_1$–$C_6$ alkyl)]$_3$, wherein n, $R_{19}$, $Q_1$, q, and $X_1$ are as defined with reference to formula I, in an appropriate solvent such as ethyl acetate at temperatures of about 0° to about 100° C. results in compounds of the formula XI wherein $R_{18}$ is $C_1$–$C_6$ alkyl, M is O, $X_1$ is $CH_2$ or a covalent bond, and $R_3$ is, respectively, ($C_1$–$C_6$ alkyl)-$(CH_2)_n$; ($C_2$–$C_8$) alkenyl-$(CH_2)_n$; and $R_{19}Q_1(CH_2)_q$—$X_1$—$(CH_2)_n$, wherein n, q, $R_{19}$, $Q_1$ and $X_1$ are as defined above.

Reaction of the compounds of the formula XI wherein M is $X_1$ is S and $R_3$ is $R_{18}$ is $C_1$–$C_6$ alkyl with amines such as $RNH_2$ or $RR_3NH$ in an appropriate solvent such as ethanol at temperatures of about 0° to about 100° C. results in compounds of the formula XI in which either or both of $R_{18}$—M and $X_1$—$R_3$ are each RNH or $NRR_3$, wherein R is as defined with reference to formula I and $R_3$ is linear alkyl, branched $C_3$–$C_8$ alkyl, or $C_3$–$C_8$ alkenyl wherein the double bond is not adjacent to the nitrogen.

The compounds of formula I wherein Z is as defined above in paragraphs (a), (h) or (i) wherein $R_5$ or $R_{14}$ is $X_2(CH_2)_rQ_2R_6$, wherein $Q_2$ is oxygen, and $X_2$, r, and $R_6$ are as previously defined except that $R_6$ is not hydrogen, may be prepared by alkylation of the corresponding compound wherein $R_5$ or $R_{14}$ are $(CH_2)_0$—$X_2$—$(CH_2)_2$—$Q_2$—$R_6$ and —$X_2$—$CH_2)_rQ_2R_6$, respectively, wherein $R_6$ is hydrogen and $Q_2$ is oxygen. In these cases wherein $R_5$ and $R_{14}$ have a terminal hydroxy group, the hydroxy is first reacted with a strong base such as an alkali metal hydride, e.g. lithium, sodium or potassium hydride, in a solvent such as dimethylformamide at about 50° to 100° C.

The resulting alkali metal alkoxide is then reacted with an alkyl or aryl sulfonyl ester of the formula $HO(CH_2)_rQ_2R_6$ wherein $R_6$ is as defined in paragraph (a) except hydrogen. This reaction is carried out in the presence of a solvent such as methylene chloride or toluene at about 50° to 100° C. The above sulfonyl esters may be prepared by the same method as described above for the activation of the compound of formula IX.

The above alkali metal hydride may be replaced by other strong bases including organometallic bases such as n-butyl lithium or amine anion bases such as lithium diisopropylamide. In such case, the metal alkoxide formation reaction may be carried out in tetrahydofuran at temperatures of about –5° to about 65° C.

The same alkylation may be used to prepare compounds of the formula I wherein $X_1$ is oxygen and $R_3$ is $(CH_2)_q$ $Q_1R_{19}$ wherein q, $Q_1$ and $R_{19}$ are as defined above with reference to formula I except that $R_{19}$ is not hydroxy, from the corresponding compounds wherein $X_1R_3$ is hydroxy.

The compounds of the formula IX wherein $R_3$ is $(CH_2)_q$ $Q_1R_6$ wherein q is as defined with reference to formula I, $Q_1$ is O and $R_6$ is methyl, react with ZH, as defined above, to form compounds of the formula

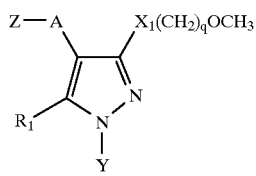

These compounds may be reacted with a demethylating agent to form the corresponding compound wherein $R_6$ is hydrogen. A suitable demethylating agent is boron tribromide in combination with sodium iodide and 15-crown-5, as described in the prior art.

The compounds of formula IA wherein A is $CH(C_1$–$C_6$ alkyl), or $CH(CH_2)_n(C_3$–$C_8$alkenyl) wherein n is 0 to 4 (having formula IB, not shown) may be prepared from the compounds of formula IX by reaction with a Grignard reagent of the formula $R_{19}MgHal$ wherein $R_{19}$ is $C_1$–$C_6$ alkyl, or $(CH_2)_n(C_3$–$C_8$ alkenyl) wherein n is 0 to 4, in a conventional manner, e.g. in diethyl ether or tetrahydrofuran solvent at about –78° to 50° C., to form a ketone of the formula

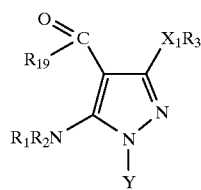

The ketone XVI may be converted to the corresponding enamine by reaction with a compound of the formula ZH wherein Z is (a) to (d) as defined above under standard acid catalyzed dehydrogenation conditions. The enamine may be converted into the compounds of formula IA wherein A is $CHR_{19}$ by hydrogenation with hydrogen under pressure in the presence of a noble metal catalyst or reduction with a hydride such as sodium or lithium cyanoborohydride in diethylether or tetrahydrofuran (THF).

Alternaively, the compounds of formula IB may be prepared from compounds IX by reaction with ZH wherein Z is (a) to (d) as defined above in the presence of a hydride reducing agent such as sodium or lithium cyanoborohydride.

The compounds of formula IA wherein A is $C(C_1$–$C_6$ alkyl)$_2$, or $C(C_1$–$C_6$ alkyl)($C_3$–$C_8$ alkenyl) may be prepared from the compound of formula IX by reaction with concentrated hydrochloric acid under reflux to form a compound of the formula

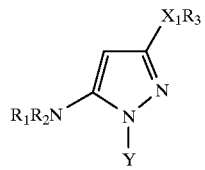

The compound XVII may be brominated, e.g. with pyridinium bromide in THF, to form the corresponding 4-bromide of formula XVIII (not shown) which may be 4-metalated in situ, such as with t-butyl lithium in diethyl ether at –78° C., and then treated in situ with an iminium compound of the formula

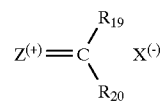

wherein $R_{19}$ is as defined above, $R_{20}$ is $R_{19}$, Z is (a) to (d) as defined above, and X is halogen.

The compounds of formula IA wherein A is $CHR_{19}$ wherein $R_{19}$ is as defined above, Z is (h) or (i) as defined above and $R^{14}$ does not have acidic hydrogens, such as hydroxyls, may be prepared from compounds of the formula I wherein Z is (h) or (i) and the other substituents are as defined above with reference to formula I by treatment with a strong base such as t-butyl lithium in ether or THF and subsequent alkylation in the same solvent with a halide of the formula $R_{19}X$ wherein $R_{19}$ and X are as defined above.

When the compounds of the invention contain a chiral center, it is understood that the invention includes the racemic mixture and the individual enantiomers of such compounds. For instance, the compounds of the invention wherein Z is 1,2,3,4-tetrahydroisoquinolinyl have a chiral center when Z is substituted at position 3 by $R_5$, wherein $R_5$ is as defined with reference to formula I except hydrogen, as follows:

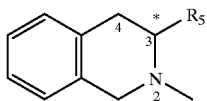

wherein the chiral center is indicated by an asterisk.

Preferred compounds of the invention of formula I include those derived from the dextrorotatory (+) enantiomer of the intermediate compound ZH of the formula

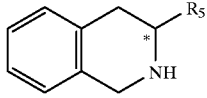

wherein $R_5$ is hydroxymethyl or ($C_1$–$C_6$ alkoxy) methyl.

The acid addition salts are prepared in a conventional manner by treating a solution or suspension of the free base of formula I or IA with one chemical equivalent of a pharmaceutically acceptable acid. Conventional concentration or crystallization techniques are employed in isolating the salts. Illustrative of suitable acids are acetic, lactic, succinic, maleic, tartaric, citric, gluconic, ascorbic, benzoic, cinnamic, fumaric, sulfuric, phosphoric, hydrochloric, hydrobromic, hydroiodic, sulfamic, sulfonic acids such as methanesulfonic, benzene sulfonic, p-toluenesulfonic, and related acids.

The novel compounds of the invention of formula I or IA may be administered alone or in combination with pharmaceutically acceptable carriers, in either single or multiple doses. Suitable pharmaceutical carriers include inert solid diluents or fillers, sterile aqueous solution and various organic solvents. The pharmaceutical compositions formed by combining the novel compounds of formula I or IA and the pharmaceutically acceptable carriers are then readily administered in a variety of dosage forms such as tablets, powders, lozenges, syrups, injectable solutions and the like. These pharmaceutical compositions can, if desired, contain additional ingredients such as flavorings, binders, excipients and the like. Thus, for purposes of oral administration, tablets containing various excipients such as sodium citrate, calcium carbonate and calcium phosphate may be employed along with various disintegrants such as starch, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerin and combinations thereof.

For parenteral administration, solutions of the novel compound of formula I in sesame or peanut oil, aqueous propylene glycol, or in sterile aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. The sterile aqueous media employed are all readily available by standard techniques known to those skilled in the art.

Additionally, it is possible to administer the compounds of the present invention topically when treating inflammatory conditions of the skin and this may be done by way of creams, jellies, gels, pastes, and ointments, in accordance with standard pharmaceutical practice.

The effective dosage for the compound of formula I or IA depends on the intended route of administration and other factors such as age and weight of the patient, as generally known to a physician. The dosage also depends on the illness to be treated. The daily dosage will generally range from about 0.1 to 50 mg/kg of the body weight of the patient to be treated. For the treatment of inflammatory diseases about 0.1 to about 100 mg/kg will be needed in general, for gastrointestinal diseases about 0.1 to about 50 mg/kg, as well as for anorexia nervosa, hemorrhagic stress, treatment of drug and alcohol withdrawal symptoms and treatment of fertility problems. The daily dosage may be given in a single dose or up to three divided doses.

The methods for testing the compounds of formula I or IA for their CRF antagonist activity are as described in Endocrinology, 116, 1653–1659 (1985) and Peptides 10, 179–188 (1989) which determine the binding activity of a test compound to a CRF receptor. The binding activity for the compounds of formula I generally ranges from about 0.2 nanomolar to about 10 micromolar.

The following Examples illustrate the invention. The designation Et means ethyl.

EXAMPLE 1

A. Ethyl 3.3-bismethylthio-2-acetylacrylate

A solution of 6.50 g (50.0 mmol) of ethyl acetoacetate and 4.18 g (3.30 mL, 55.0 mmol) of carbon disulfide in 60 mL of dry dimethylsulfoxide in a flame-dried 300 mL flask was treated portionwise at 16–18° C. with 2.64 g (110 mmol) of oil-free sodium hydride. An additional 100 mL of dimethylsulfoxide was eventually added to facilitate stirring. After the addition was complete, the deep red solution was stirred for 75 minutes and then was quenched with 15.62 g (6.85 mL, 110 mmol) of methyl iodide. The reaction mixture was stirred overnight at room temperature. The solution was poured into water and extracted with ether. The extracts were washed with water, dried and evaporated to give a red oil which was used for subsequent reactions without further purification. $^1$H-NMR (CDCl$_3$) δ1.24 (3H, t, J=7), 2.28 (3H, s), 2.37 (6H, s), 4.21 (2H, q, J=7).

B. 4-Ethoxycarbonyl-5-methyl-3-methylthio-1-(2,4,6-trichlorophenyl)pyrazole

A mixture of 1.22 g (5.23 mmol) of ethyl 3,3-bismethylthio-2-acetylacrylate and 1.11 g (5.23 mmol) of 2,4,6-trichlorophenylhydrazine in 12 mL of ethanol was heated at reflux for 2 hours. The cooled reaction mixture was then poured into cold water and the product was extracted into ether. The ethereal extracts were dried and evaporated and the residues were chromatographed on silica gel using 6:1 hexane/ethyl acetate as eluent to give 1.12 g (56%) of the desired product as a crystalline solid, m.p. 95–98° C. $^1$H-NMR (CDCl$_3$) δ1.38 (3H, t, J=7), 2.30 (3H, s), 2.49 (3H, s.), 4.31 (2H, q, J=7), 7.47 m(2H, s).

C. 2-(5-Methyl-3-methylthio-1-(2,4,6-trichlorophenyl) pyrazol-4-yl)methyl-1,2,3,4-tetrahydroisoquinoline.

A solution of 0.340 g (0.89 mmol) of 4-ethoxycarbonyl-5-methyl-3-methylthio-1-(2,3,6-trichlorophenyl)pyrazole in 10 mL of tetrahydrofuran was cooled to 0° C. in an ice bath under dry nitrogen and then 2.37 mL of a 1.5 M solution of diisobutylaluminum hydride in toluene (3.56 mmol) was added. The reaction mixture was allowed to warm to room temperature and stir for 2 hours. Then water was added cautiously and the product was extracted into ether which was dried and evaporated to give the product which was used for the subsequent reaction without further purification. $^1$H-NMR (CDCl$_3$) δ2.07 (3H, s), 2.53 (3H, s), 4.56 (2H, d, J=7), 7.45 (2H, s).

The above product was dissolved in 10 mL of methylene chloride and 0.62 mL (0.45 g, 4.45 mmol) of triethylamine at 0–5° C. and treated with 0.21 mL (0.31 g, 2.67 mmol) of methanesulfonyl chloride. After 1 hour at room temperature, the reaction mixture was poured into water and was extracted with ethyl acetate. The solution of product was dried with brine and magnesium sulfate and the solvent was evaporated to give the intermediate mesylate which was used in the subsequent step without further purification.

The product of the above reaction (0.98 mmol) was dissolved in 10 mL of acetonitrile and treated with 0.45 mL (0.475 g, 3.57 mmol) of 1,2,3,4-tetrahydroisoquinoline. The solution darkened and then lightened over a period of a few minutes and was then stirred overnight at room temperature. Solids which had formed were filtered off and discarded and the filtrate was concentrated and chromatographed on silica gel using 4:1 hexane/ethyl acetate as eluent to give the product free base. This material was dissolved in ether and treated with a solution of hydrogen chloride (gas) in ether to give the product hydrochloride, m.p. 205–207° C. (53% over the three reactions). Anal. Calcd for C$_{21}$H$_{20}$N$_3$SCl$_3$: C, 51.55; H, 4.33; N, 8.59. Found, C, 51.01; H, 4.69; N, 8.40.

EXAMPLE 2

The following compounds were prepared by the process of Example 1.

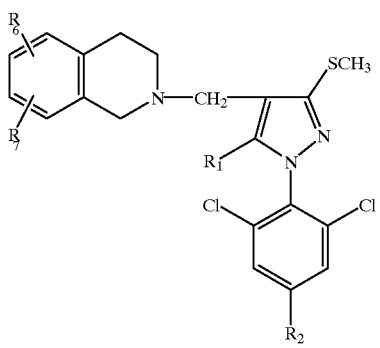

| R$_1$ | R$_2$ | R$_6$ | R$_7$ | Physical data (m.p. in ° C.) |
|---|---|---|---|---|
| CH$_3$ | Cl | H | H | m.p. 20–207 |
| CH(CH$_3$)$_2$ | Cl | H | H | m.p. 20–210 |
| CH(CH$_3$)$_2$ | Cl | OCH$_3$ | OCH$_3$ | m.p. 14–142 |
| phenyl | CF$_3$ | H | H | $^1$H-NMR(CDCl$_3$) δ 2.59 (s, 3H), 2.74 (2H, t, J=7), 2.89 (2H, t, J=7), 3.54 (2H, s), 3.64 (2H, s), 6.98–7.01 (1H, m), 7.07–7.15 (3H, m), 7.2–7.32 (3H, m), 7.37–7.42 (2H, m), 7.60 (2H, m). |

EXAMPLE 3

A. 4-Methoxycarbonyl-3,5-heptanedione

A solution of 6.5 g (50 mmol) of methyl propionyl acetate in 100 mL of ether was treated with 1.19 g (50 mmol) of sodium hydride and the mixture was stirred for 2 hours. The mixture was then cooled to 5° C. and 6.93 g (6.51 mL. 75 mmol) of propionyl chloride was added dropwise over 5 minutes. The reaction mixture was stirred overnight at room temperature and then poured into cold water. This mixture was acidified with sulfuric acid and the product was extracted into ether, washed with water and dried. Evaporation gave the desired product, sufficiently pure for use in the following reaction, in 88% yield. $^1$H-NMR (CDCl$_3$) δ1.08 (6H, t, J=7), 2.58 (4H, q, J=7), 3.66 (1H, s), 3.74 (3H, s).

B. Methyl 1-(2,6-dichloro-4-trifluoromethylphenyl)-3,5-diethylpyrazole-4-carboxylate.

A solution of 7.5 g (40 mmol) of the compound of step A and 11.85 g (48 mmol) of 2,6-dichloro-4-trifluoromethylphenyl hydrazine in 50 mL of ethanol was heated at reflux for 8 hours. The ethanol was removed by evaporation and the residues were partitioned between ethyl acetate and dilute hydrogen chloride. The organic extracts were dried and evaporated to give the desired product in 43% yield as a maroon oil. $^1$H-NMR (CDCl$_3$) δ1.08 (3H, t, J=7), 1.24 (3H, t, J=7), 2.22 (2H, q, J=7), 2.94 (2H, q, J=7), 3.86 (3H, s), 7.46 (2H, s).

C. [1-(2,6-Dichloro-4-trifluoromethylphenyl)-3,5-diethyl-1H-pyrazol-4-yl]methanol.

A solution of 8 g (20 mmol) of the compound of step B in 50 mL of tetrahydrofuran (THF) was treated at ° C. with 44.1 mL of 1.5 M diisobutylaluminum hydride in toluene solution over a period of 5 minutes. The reaction was stirred for 2 hours at ° C. and was then cautiously quenched with water. The product was extracted into ethyl acetate and dried and evaporated to give the title compound in 46% yield. $^1$H-NMR (CDCl$_3$) δ1.04 (3H, t, J=7), 1.26 (3H, t, J=7), 2.44 (2H, q, J=7), 2.70 (2H, q, J=7), 4.54 (2H, s), 7.66 (2H, s).

D. 1 [3,5-Diethyl-1-(2,6-dichloro-4-trifluoromethylphenyl)-1H-pyrazol-4-ylmethyl]naphthalen-2-ol.

A solution of 303 mg (2.1 mmol) of 2-naphthol in 5 mL of dry ether was treated with 50 mg (2.1 mmol) of sodium hydride and the mixture was stirred for 15 minutes. A solution of 368 mg (1.0 mmol) of the compound of step C in 5 mL of dry ether and 126 mg (0.174 mL, 1.22 mmol) of triethylamine was cooled to 0° C. and treated with 114 mg (0.077 mL, 1.0 mmol) of methanesulfonyl chloride. Triethylamine hydrochloride was removed by filtration and the filtrate was added to the above suspension of sodium 2-naphthoxide and the reaction mixture was stirred at room temperature for 12 hours. The reaction mixture was then partitioned between water and ether and the organic extracts were dried and evaporated to give the desired product in 29% yield. $^1$H-NMR (CDCl$_3$) δ1.00 (3H, t, J=7), 1.20 (3H, t, J=7), 2.44 (2H, q, J=7), 2.72 (2H, q, J=7), 4.58 (2H, s), 6.96–7.84 (8H, m).

E. 3,5-Diethyl-4-(2-methoxynaphthalen-1-ylmethyl)-1-(2,6-dichloro-4-trifluoromethylphenyl)-1H-pyrazole.

A solution of 100 mg (0, 20 mmol) of the compound at step D in 5 mL of dry THF was treated with 5 mg (0.20 mmol) of sodium hydride and stirred for 15 minutes. Then 85 mg (0.037 mL, 0.60 mmol) of methyl iodide was added and the mixture was stirred overnight at room temperature. The reaction mixture was quenched with water and the product was extracted into ethyl acetate, dried and evaporated. Flash column chromatography gave the desired product as a white solid, m.p. 96–98° C. $^1$H-NMR (CDCl$_3$) δ0.6 (3H, t, J=7), 1.04 (3H, t, J=7), 206 (2H, q, J=7), 251 (2H, q, J=7), 3.90 (3H, s), 4.14 (2H, s), 7.18–7.34 (3H, m), 7.58 (2H, s, 7.70–7.84 (3H, m).

EXAMPLE 4

8-[1-(2,6-Dichloro-4-trifluoromethylphenyl)-3,5-diethyl-1H-pyrazol-4-ylmethyl]-quinolin-7-ol By the general method of Example 3D, substituting 7-hydroxisoquinoline for 2-naphthol, the title compound was prepared [45 mg of an oil, isolated after flash chromatography (silica gel, 40 micron mesh; elution with ethylacetate/hexane=1:4 in volume), from reaction utilizing 264 mg (0.75 mmol) of the compound of Example 3C as starting material. $^1$H-NMR(CDCl$_3$): 0.83 (3H, t), 1.09 (3H, t), 2.37 (2H, q), 2.50 (2H, q), 4.64 (2H, s), 7.14 (1H, d), 7.30 (1H, dd), 7.64 (1H, d), 770 (2H, s).

EXAMPLE 5

A. 2-{1-[1-(2,6-Dichloro-4-trifluoromethylphenyl)-3,5-diethyl-1H-pyrazol-4-ylmethyl]-napthalen-2-yloxy}-ethanol tert-butyl-dimethylsilylether To a tetrahydrofuran (1.0 ml) solution of the compound of Example 3D (150 mg, 0.30 mmol), sodium hydride (37 mg of 60% sodium hydride mineral oil dispersion; 22.2 mg, 0.93 mmol of sodium hydride) was added portionwise over several minutes; 1-iodo-2-(tert-butyldimethylsilyloxy)ethane (858 mg, 0.30 mmol) was added, and the reaction was stirred and heated at 45° C. for 48 hours. An additional (858 mg, 0.30 mmol) portion of 1-iodo-2-(tert-butyldimethylsilyloxy)ethane was added; and the reaction was then heated at 45° C. for an additional 18 hours. The solvent was removed in vacuo, and the residue was extracted into ethyl acetate/water (100 ml of each). The separated aqueous layer was extracted twice with 30 ml portions of ethyl acetate. The combined organic extracts were dried (anhydrous sodium sulfate) and concentrated in vacuo to an oil (1.95 g). Flash chromatography of the entire sample (silica gel, 40 micron mesh; elution with ethyl acetate/hexane=5:95 in volume) afforded the title compound (40 mg) as an oil. $^1$HNMR(CDCl$_3$): 0.10(6H, s), 0.60 (3H, t), 0.90 (9H, s), 1.10 (3H, t), 2.10 (2H, q), 2.56 (2H, q), 4.00 (2H, q), 4.20 (2H, q), 4.32 (2H, s), 7.25–7.38 (3H, m), 7.65 (2H, s), 7.73–7.87 (3H, m).

B. 2-{1-[1-(2,6-Dichloro-4-trifluoromethylphenyl)-3,5-diethyl-1H-pyrazol-4-ylmethyl]-napthalen-2-yloxy}-ethanol A tetrahydrofuran (0.40 ml) solution of the compound of step A, (40 mg, 0.06 mmol) and tetrabutylammonium fluoride (123 μl of a 1.00 M tetrahydrofuran (THF) solution, 0.123 mmol) was stirred at ambient temperature for 3 hours. The solvent was removed in vacuo, and the residue was extracted into ethyl acetate/water (60 ml of each). The separated organic phase was extracted twice with equal volume portions of water, dried over anhydrous sodium sulfate, and concentrated in vacuo to an oil (49 mg). Flash chromatography of the entire sample (silica gel, 40 micron mesh; elution with ethylacetate/hexane=3:7 in volume) afforded the title compound (24 mg) as an amorphous solid. $^1$H-NMR(CDCl$_3$): 0.58(3H,t), 1.15 (3H, t), 1.99 (1H, broad), 2.07 (2H, q), 2.58 (2H, q), 3.99 (2H, m), 4.23 (2H, t), 4.32 (2H, s), 7.2–7.45 (3H, overlapping multiplets), 7.66 (2H, s), 7.80 (2H, dd), 7.91 (1H, d).

EXAMPLE 6

A. {2-[1-(2,6-Dichloro-4-trifluoromethylphenyl)-3,5-diethyl-1H-pyrazol-4-ylmethyl]-1,2,3,4-tetrahydroisoquinolin-3-yl}methanol A solution of 368 mg (1.0 mmol) of [1-(2,6-dichloro-4-trifluoromethylphenyl)-3,5-diethyl-1H-pyrazol-4-yl]methanol in 10 mL of methylene chloride and 0.2 mL (2.5 mmol) of triethylamine was cooled to 0–5° C. To this was added 0.92 mL (1.2 mmol) of methanesulfonyl chloride and the reaction mixture was stirred at 0–5 ° C. for 15 minutes. Then 1 mL of acetonitrile and 1 mL of dimethylformamide was added and the reaction mixture was heated at reflux overnight. The cooled reaction mixture was taken up with water and with ethyl acetate and the organic extracts were dried and evaporated to an orange oil which was purified by flash chromatography to give the desired product in 45% yield. $^1$H-NMR (CDCl$_3$) δ0.86 (3H, t, J=7), 1.21 (3H, t, J=7), 2.28 (2H, q, J=7), 2.60 (2H, q, J=7), 2.92–3.04 (1H, m), 3.20–3.32 (1H, m), 3.50–3.90 7H, m), 6.90–7.24 (4H, m), 7.68 (2H, s).

B. 2-[-1-(2,6-Dichloro-4-trifluoromethylphenyl)-3,5-diethyl-1H-pyrazol-4-ylmethyl]-3-methoxymethyl-1,2,3,4-tetrahydroisoquinoline A solution of 200 mg (0.39 mmol) of the compound of step A in 5 mL of THF was treated with 10 mg (0.42 mmol) of sodium hydride and stirred for 30 minutes at room temperature. Then 0.1 mL (1.6 mmol) of methyl iodide was added and the reaction mixture was stirred at room temperature for 24 hours. The reaction was quenched with water and the product was extracted into ethyl acetate which was dried and evaporated. The crude product was flash chromatographed on silica gel to give the desired product in 26% yield as a colorless oil. $^1$H-NMR (CDCl$_3$) δ0.90 (3H, t, J=7), 1.20 (3H, t, J=7), 2.39 (2H, q, J=7), 2.65 (2H, q, J=7), 2.88–2.96 (1H, m), 3.16–3.20 (1H, m), 3.32 (3H, s), 3.55–3.78 7H, m), 6.90–7.24 (4H, m), 7.65 (2H, s).

EXAMPLE 7

The following compounds were prepared according to the process of Example 6.

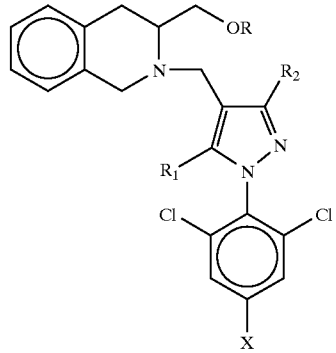

| | R | $R_1$ | $R_2$ | X | $^1$H-NMR |
|---|---|---|---|---|---|
| Racemate | H | CH$_3$ | SCH$_3$ | Cl | (CDCl$_3$) δ 1.84 (3H, s), 2.48 (3H1 s), 2.88 (2H, d of d, J=7,7), 3.22 (1H, m), 3.40–3.66 (5H, m), 3.79 (1H, d, J=7), 6.88–7.14 (4H, m), 7.40 (2H, s). |
| Racemate | CH$_3$ | CH$_3$ | SCH$_3$ | Cl | (CDCl$_3$) δ 1.96 (3H, s), 2.46 (3H, s), 2.80 (1 H, ab quartet, J=7.2), 2.82 (1H, ab quartet, J=7, 20), 3.6 (1H, m), 3.32 (3H, s), 3.34–3.74 (6H, m), 6.88–7.10 (4H, m), 7.40 (2H, s). |

-continued

| | R | R₁ | R₂ | X | ¹H-NMR |
|---|---|---|---|---|---|
| Enantiomer | H | CH₃ | SCH₃ | Cl | (CDCl₃) δ 1.80 (3H, s), 2.48 (3H, s), 2.88 (2H, d of d, J=7.7), 3.20 (1H, m), 3.40–3.66 (5H, m), 3.79 (1H, d, J=7), 6.88–7.14 (4H, m), 7.40 (2H, s). |
| Enantiomer | CH₃ | CH₃ | SCH₃ | Cl | (CDCl₃) δ 1.96 (3H, s), 2.46 (3H, s), 2.80 (1H, ab quartet, J=7.20), 2.82 (1H, ab quartet, J=7.20) 3.16 (1H, m), 3.32 (3H, s), 3.34–3.74, (6H, m), 6.88–7.10 (4H, m), 7.40 (2H, s). |
| Racemate | H | CH₃ | SCH₃ | CF₃ | (CDCl₃) δ 2.06 (3H, s), 2.24 (3H, s), 2.70 (1H, ab quartet, J=7, 30), 2.72 (1H, ab quartet, J=7, 30), 3.20 (1H, m), 3.50–3.80 (6H, m), 6.88–7.12 (4H, m), 7.65 (2H, s). |
| Racemate | CH₃ | CH₃ | SCH₃ | CF₃ | (CDCl₃) δ 2.12 (3H, s), 2.32 (3H, s), 2.78 (1H, ab quartet, J=7, 16), 2.80 (1H, ab quartet, J=7, 16), 3.18 (1H, m), 3.30 (3H, s), 3.50–3.90 (6H, m), 6.92–7.16 (4H, m), 7.64 (2H, s). |
| Racemate | H | Et | Et | Cl | (CDCl₃) δ 0.84 (3H, t, J=7), 1.22 (3H, t, J=7), 2.28 (2H, q, J=7), 2.60 (2H, q, J=7), 2.66 (1H, d of d, J=7, 15), 3.26 (1H, m), 3.50–3.86 (6H, m), 6.96–7.08 (4H.9 m), 7.42 (2H, s). |
| Racemate | CH₃ | Et | Et | Cl | (CDCl₃) δ 0.92 (3H, t, J=7), 1.20 (3H, t, J=7), 2.38 (2H, q, J=7), 2.66 (2H, q, J=7), 2.80 (1H, ab quartet, J=7, 40), 2.82 (1H, ab quartet, J=7, 40), 3.16 (1H, m), 3.34 (3H, s), 3.35–3.74 (6H, m), 6.92–7.10 (4H, m), 7.40 (2H, s). |
| Enantiomer | H | Et | Et | Cl | (CDCl₃) δ 0.86 (3H, t, J=7), 1.20 (3H, t, J=7), 2.26 (2H, q, J=7), 2.58 (2H, q, J=7), 2.54 (1H, d of d, J=7, 15), 2.95 (1H, d of d, J=7, 15), 3.24 (1H, m), 3.48–3.84 (6H, m), 6.90–7.08 (4H, m), 7.40 (2H, s). |

EXAMPLE 8

The following compounds were prepared according to Examples 3 and 5.

| R | R₁ | R₂ | X | ¹H-NMR |
|---|---|---|---|---|
| CH₃ | CH₃ | SCH₃ | Cl | (CDCl₃) δ 1.48 (3H, s), 2.46 (3H, s), 3.92 (3H, s), 4.14 (2H, s), 7.18–7.38 (3H, m), 7.32 (2H, 5), 7.68–7.88 (3H, m). |
| CH₃ | Et | Et | CF₃ | (CDCl₃) δ 0.60 (3H, t, J=7), 1.04 (3H, t, J=7), 2.08 (2H, q, J=7), 2.46 (2H, q, J=7), 3.90 (3H, s), 4.26 (2H, 5), 7.16–7.34 (3H, m), 7.58 (2H, s), 7.70–7.84 (3H, m). |
| H | CH₃ | CH₃ | Cl | (CDCl₃) δ 1.80 (3H, s), 2.10 (3H, s), 4.20 (2H, s), 6.98 (1H, d, J=7), 7.26 (1H, t, J=7), 7.36 (2H, s), 7.37 (1H, t, J=7), 7.55 (1H, d, J=7), 7.72 (1H, d, J=7), 7.78 (1H, d, J=7). |
| CH₃ | CH₃ | CH₃ | Cl | (CDCl₃) δ 1.75 (3H, s), 2.06 (3H, s), 3.94 (3H, s), 4.23 (2H, s), 7.21–7.40 (3H, m), 7.40 (2H, s), 7.71–7.86 (3H, m). |
| CH₃ | Et | Et | CF₃ | (CDCl₃) δ 0.6 (3H, t. J=7), 2.06 (3H, t, J=7), 2.08 (2H, q, J=7), 2.46 (2H, q, J=7), 3.90 (3H, s), 4.24 (2H, s), 7.18–7.36 (2H, m), 7.60 (2H, s), 7.71 (2H, d, J=8), 7.81 (2H, d, J=8). |

EXAMPLE 9

A. 3,5-Diethyl-1-(2,4,6-trimethylphenyl)pyrazole.

A solution of 7.46 g (0.04 mol) of 2,4,6-trimethylphenylhydrazine hydrochloride, 5.12 g (0.40 mol) of 3,5-heptanedione and 4.18 mL (0.60 mol) of triethylamine in 100 mL of absolute ethanol was refluxed overnight. The solvent was evaporated from the cooled reaction mixture and the residues were partitioned between water and ethyl acetate. The organic extracts were dried with brine and magnesium sulfate, and the solvent was evaporated to give the desired product in 95% yield. This compound was used in the subsequent reaction without further purification ¹H-NMR (CDCl₃): 0.11 (3H, t, J=7), 1.24 (3H, t, J=7), 1.90 (6H, s), 2.22 (2H, q, J-7), 2.28 (3H, s), 2.65 (2H, q, J=7), 5.96 (1H, s), 6.86 (2H, s).

B. 4-Bromo-3,5-diethyl-1-(2,4,6-trimethylphenyl)pyrazole.

A solution of 6.4 g (0.04 mol) of bromine in 20 mL of glacial acetic acid was added dropwise to a stirred solution of 9.00 g (37 mmol) of 3,5-diethyl-1-(2,4,6-trimethylphenyl)pyrazole in 100 mL of glacial acetic acid. After 1 hour at room temperature, the acetic acid was evaporated under reduced pressure and the residues were dissolved in ethyl acetate. This solution was washed with saturated sodium bicarbonate to remove residual acetic acid, dried with brine and magnesium sulfate, and was concentrated on the rotovap. The product was a tan solid (10.26 g, purification. $^1$H-NMR(CDCl$_3$):0.92 (3H, t, J=7), 1.15 (3H, t, J=7), 1.86 (6H, s), 2.24 (3H, s), 2.32 (2H, q, J=7), 2.60 (2H, q, J=7), 6.82 (2H, s).

C. 3,5-Diethyl-1-(2,4,6-trimethylphenyl)pyrazole-4-methanol.

A solution of 1.0 g (3.1 mmol) of 4-bromo-3,5-diethyl-1-(2,4,6-trimethylphenyl)pyrazole in 10 mL of anhydrous ether in a flame-dried 3-neck round bottom flask under dry nitrogen with 3.85 mL of 1.7 m t-butyllithium in pentane. After 1 hour, the reaction mixture was treated with 0.355 mL of ethyl chloroformate and was then allowed to warm to room temperature. The reaction mixture was quenched with water and then ethyl acetate was added. The aqueous layer was extracted with ethyl acetate again and the organic extracts were combined and dried with brine and magnesium sulfate and then the solvent was removed on the rotovap. This product, 3,5-diethyl-4-ethoxycarbonyl-1-(2,4,6-trimethylphenyl)pyrazole, was determined to be 59% pure by gas chromatographic (GC) analysis.

This material, approximately 3.1 mmol, was dissolved in 10 mL of ether and cooled under dry nitrogen to 0° C. Then 7 mL (10 mmol) of 1.5M diisobutylaluminum hydride in tulene was added over about 10 minutes. The reaction mixture was stirred at 0° C. until no starting material was observed by GC and was then quenched with water. The product was extracted into ethyl acetate, dried with brine and magnesium sulfate, and concentrated. The residues were flash chromatographed on silica gel using 4:1 and 1:1 hexane/ethyl acetate as eluent to give the desired product as an oil in the amount of 0.565 g (69% yield for the two reactions). $^1$H-NMR (CDCl$_3$):0.94 (3H, t, J=7), 1.23 (3H, t, J=7), 1.88 (6H, s), 2.26 (3H, s), 2.35 (2H, 1, J=7), 2.66 (2H, q, J=7), 4.50 (2H, s), 6.82 (2H, s).

D. {2-[3,5-Diethyl-1-(2,4,6-trimethylphenyl)-1H-pyrazol-4-ylmethyl]-1,2,3,4-tetrahydroisoquinolin-3-yl}methanol.

To a solution of 272 mg (1.0 mmol) of 3,5-diethyl-1-(2, 4,6-trimethylphenyl)pyrazole-4-methanol in 5 mL of methylene chloride cooled to 0° C. under dry nitrogen in a 25 mL 3-neck flask, was added to 0.2 mL (2.5 mmol) of triethylamine and 0.092 mL (2.0 mmol) of methanesulfonyl chloride. This mixture was stirred for 15 minutes at 0° C. and then 0.648 g (4.0 mmol) of (+)-3-hydroxymethyl-1,2,3,4-tetrahydroisoquinoline in 1 mL of 50:50 dimethylformamide acetonitrile was added. The reaction mixture was heated at reflux overnight whereupon no starting material was seen by TLC. The cooled reaction mixture was diluted with water and the product was extracted with ethyl acetate. After drying (brine wash, magnesium sulfate) and evaporation, the crude product was chromatographed on silica gel, eluting with 10:1 and 5:1 hexane/ethyl acetate to give 184 mg (44%) of the desired product. $^1$H-NMR (CDCl$_3$):0.80 (3H, t, J=7), 1.18 (3H, t, J=7), 1.92 (6H, s), 2.21 (2H, q, J=7), 2.28 (3H, s), 2.55 (2H, q, J=7), 2.97 (2H, d of d, J=7), 3.25 (1H, m), 3.50–3.66 (5H, m), 3.38 (2H, d, J=12), 6.82–7.16 (6H, m).

E. 2-[3,5-Diethyl, 1,(2,4,6-trimethylphenyl)-1H-pyrazol-4-ylmethyl]-3-methoxymethyl-1,2,3,4-tetrahydroisoquinoline.

A solution of 150 mg (0.36 mmol) of {2-[3,5-diethyl-1-(2,4,6-trimethylphenyl)-1H-pyrazol-4-ylmethyl]-1,2,3,4-tetrahydroisoquinolin-3-yl}methanol in 5 mL of THF was stirred under dry nitrogen as 11 mg (0.43 mmol) of oil-free sodium hydride was added. The reaction mixture was stirred for 15 minutes and then 0.044 mL (0.72 mmol) of methyliodide was added. The reaction mixture was stirred overnight and then diluted with water. The product was extracted into ethyl acetate and the organic extracts were dried with brine and magnesium sulfate, and evaporated. The product was isolated pure by chromatography on silica gel using 10:1 and 5:1 hexane/ethyl acetate as eluent to give 84 mg (52%) of a golden oil. $^1$H-NMR (CDCl$_3$):0.86 (3H, t, J=7), 1.20 (3H,t,J=7), 1.92 (6H, s), 2.28 (3H, s), 2.32 (2H, q, J=7), 2.63 (2H, q, J=7) 2.83 (2H, d of ABq), 3.17 (1H, m), 3.33 (3H, s), 3.34–3.38 (1H, m), 3.54–3.76 (5H, m), 6.83–7.16 (6H, m).

The following examples illustrate the preparation of intermediates.

Preparation 1

Racemic (1,2,3,4-Tetrahydro-isoquinolin3-yl-methanol [also referred to as (±)-3-hydroxymethyl-1,2,3,4-tetrahydroisoquinoline To a well stirred, ice-bath-chilled slurry of 1,2,3,4-tetrahydroisoquinoline-3-carboxylic acid hydrochloride (75 g, 0.351 mol. Aldrich Chemical Co.) in anhydrous methanol (600 ml), sodium methoxide (37.92 g, 0.702 mol) was added in small solid portions over a 10 minute period. After 30 minutes of brisk stirring, the methanol was removed and the colorless residue was dried in vacuo overnight. The entire sample was stirred in anhydrous tetrahydrofuran causing the organic portion to dissolve completely. A 1.0 M solution of lithium aluminum hydride in tetrahydrofuran (351 ml, 0.351 mol) was added in a rapid stream to the well-stirred mixture over a 20 minute period (mild exotherm). The reaction mixture was then vigorously refluxed for 2 hours. At 5° C., the reaction was quenched by cautious addition of 15% aqueous sodium hydroxide. The mixture was filtered, and the filtrate was concentrated in vacuo to a yellow solid. The entire sample was then dissolved in methylene chloride (400 ml) and filtered to remove residual inorganic salts. Solvent removal in vacuo afforded the title compound as an orange solid (47.01 g, 70% yield). TLC R$_1$ (silica gel plates, u.v. detection, methanol/methylene chloride=5:95 in volume): 0.46; $^{13}$C NMR(CDCl$_3$): 135.4, 134.1, 129.3, 126.3, 126.1, 125.9, 65.4, 55.0, 47.8, 30.9.

Preparation 2

Dextrorotatoryenantiomer of (1,2,3,4-Tetrahydro-isoquinolin-3-yl)-methanol (also referred to as (+)-3-hydroxymethyl-1,2,3,4-tetrahydroisoquinoline)

To a solution of (±)-3-hydroxymethyl-1,2,3,4-tetrahydroisoquinoline (Preparation 1; 47.01 g, 0.288 mol) in isopropyl alcohol (159 ml), a solution of (S)-(+)-mandelic acid -(43.81 g, 0.288 mol) in isopropyl alcohol (159 ml) was added. The resulting solution was allowed to stand at ambient temperature for 48 hours, during which time a heavy orange crystalline mass formed. The isolated crystalline solid (13.06 g) was dissolved in hot isopropyl alcohol (63 ml). After standing for 1 hour at ambient temperature, the newly-formed crystalline solid was isolated by filtration (8.2 g, m.p. 138° C.). The recrystallization procedure was repeated twice more, using 63 ml and 60 ml volumes of isopropyl alcohol to afford 7.08 g and 6.76 g of crystalline material, respectively. (In each case, the crystallization was allowed to proceed for 2 hours at ambient temperature prior to filtration.) A 138–139° C. m.p. was observed after the final crystallization. The entire sample was dissolved in methylene chloride water (300 ml and 100 ml, respectively) with the pH adjusted to 9.5 (potassium carbonate). The phases were separated, and the aqueous portion was extracted with three 50 ml portions of fresh methylene chloride. The combined organic extracts were dried (anhydrous sodium sulfate) and concentrated in vacuo to afford the optically resolved title compound as a colorless amorphous solid (2.02 g, 8.6% yield). $[\alpha]^{20}_D$+103° (c=1.83, $CH_2Cl_2$); $^{13}C$ NMR ($CDCl_3$): identical to that of the racemic compound prepared in Preparation 1.

Preparation 3

Levorotatory enantiomer of (1,2,3,4-Tetrahydro-isoquinolin-3-yl)-methanol [also referred to as (−)-3-hydroxymethyl-1,2,3,4-tetrahydroisoquinoline]

Substituting (R)-(−)-mandelic acid for (S)-(+)-mandelic acid in the Preparation 2 procedure (and utilizing 17.9 g of the alcohol-amine prepared in Preparation 1), the levorotary title compound (0.65 g, 7.3% yield) was obtained as a colorless amorphous solid. $[\alpha]^{20}_d$−100.4° ($CH_2Cl_2$, c=1.43; $^1H$ NMR and $^{13}C$ NMR ($CDCl_3$): identical in all respects to those observed for the racemic (Preparation 1) and dextrorotatory (Preparation 2) products.

Preparation 4

Methyl 3,5-diethyl-1-(2,4,6-trichlorophenyl)pyrazole-4-carboxylate

A mixture of 11.0 g (60.0 mmol) of methyl 2-propionyl-3-ketopentanoate and 11.26 g (65.0 mmol) of 2,4,6-trichlorophenylhydrazine in 50 mL of ethanol was refluxed under nitrogen until disappearance of starting material was noted. The solvent was removed in vacuo and the residues were partitioned between ethyl acetate and dilute hydrogen chloride. The organic layer was dried and evaporated to give the product as an off-white solid which was used for subsequent reactions without further purification. $^1$H-NMR: ($CDCl_3$) δ1.02 (3H, t, J=7), 1.21 (3H, t, J=7), 2.62 (2H, q, J=7), 2.86 (2H, q, J=7), 3.82 (3H, s), 7.42 (2H, s).

We claim:

1. A compound of the formula

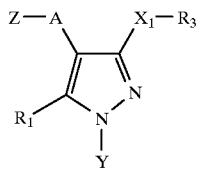

I or the pharmaceutically acceptable acid addition salts thereof, wherein

A is $CH_2$;

$R_1$ is hydrogen; linear or branched $C_1$–$C_6$ alkyl; $C_3$–$C_6$ alkyl containing one or two non-adjacent double bonds; hydroxy; O($C_1$–$C_6$ alkyl); SH; S($C_1$–$C_6$ alkyl); or $C_3$–$C_6$ cycloalkyl; morpholinyl, piperdinyl or aryl which aryl may be substituted by one to three of fluoro, chloro, bromo, hydroxy, O($C_1$–$C_6$ alkyl), SH, S($C_1$–$C_6$ alkyl), amino, NH($C_1$–$C_6$ alkyl), N($C_1$–$C_6$ alkyl)$_2$, or one of iodo, nitro or cyano, said aryl being selected from the group consisting of phenyl, thienyl, benzothienyl, pyridyl, quinolyl, pyrazinolyl, pyrimidyl, imidazolyl, benzimidazolyl, furanyl, benzofuranyl, thiazolyl, benzothiazolyl, isothiazolyl, benzoisothiazolyl, isoxazolyl, benzisoxazolyl, triazolyl, pyrazolyl, pyrrolyl, indolyl, azaindolyl, oxazolyl, benzoxazolyl, pyrrolidinyl, or thiazolidinyl;

$R_3$ is linear $C_1$–$C_6$ alkyl, branched $C_3$–$C_8$ alkyl, $C_3$–$C_8$ alkenyl wherein the double bond is not adjacent to $X_1$ when $X_1$ is a heteroatom, $C_3$–$C_7$ cycloalkyl($CH_2$)$_n$ wherein n is 0 to 4, or ($CH_2$)$_q$$Q_1$$R_{19}$ wherein q is 0, 1 or 2, $Q_1$ is O, S, NH, N($C_1$–$C_6$ alkyl), or a covalent bond when $X_1$ is not a covalent bond, and $R_{19}$ is hydrogen, linear $C_1$–$C_6$ alkyl, branched $C_3$–$C_8$ alkyl, $C_3$–$C_8$ alkenyl, $C_3$–$C_6$ cycloalkyl or $C_3$–$C_6$ cycloalkyl-($CH_2$) with the proviso that when q is 1, then $X_1$ and $Q_1$ cannot both be a heteroatom;

$X_1$ is a covalent bond, $CH_2$, O, S, or NR, wherein R is hydrogen, linear $C_1$–$C_6$ alkyl or branched $C_3$–$C_8$ alkyl;

Y is phenyl, thienyl, benzothienyl, pyridyl, quinolyl, pyrazinolyl, pyrimidyl, imidazolyl, benzimidazolyl, furanyl, benzofuranyl, thiazolyl, benzothiazolyl, isothiazolyl, benzisothiazolyl, isoxazolyl, benzisoxazolyl, triazolyl, pyrazolyl, pyrrolyl, indolyl, azaindolyl, oxazolyl, benzoxazolyl, pyrrolidinyl, thiazolidinyl, morpholinyl, or piperidinyl, each of which may be substituted by one to three of any one of fluoro, chloro, bromo, or methyl, or one of trifluoromethyl; with the proviso that Y is not unsubstituted phenyl; and Z is

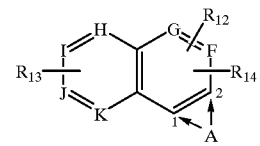

VII wherein A is defined above and is linked to position 1 or 2 while $R_{14}$ is attached to position 2 or 1, respectively; F, G, H, I, J and K are independently C or N, provided that not more than three of H, I, J and K are N with not more than two adjacent nitrogens; $R_{12}$ and $R_{13}$ each independently are hydrogen, linear $C_1$–$C_6$ alkyl, branched $C_3$–$C_8$ alkyl, $C_3$–$C_8$ alkenyl, fluoro, chloro, bromo, trifluoromethyl, hydroxy, thiol, $C_1$–$C_{12}$ alkoxy, $C_1$–$C_{12}$ thioalkanyl, or $C_3$–$C_{12}$ alkenoxy or $C_3$–$C_{12}$ thioalkenyl wherein the double bond is not adjacent to the oxygen; and $R_{14}$ is hydroxy, $C_1$–$C_{12}$ alkoxy, $C_3$–$C_{12}$ alkenoxy wherein the double bond is not adjacent to the oxygen, or —$X_2$—($CH_2$)$_r$$Q_2$$R_6$ wherein $X_2$, is O,S, NH, N($C_1$–$C_8$ alkyl), $Q_2$ is O, NH, N($C_1$–$C_6$ alkyl), or one of $X_2$ and $Q_2$ may be a covalent bond; and r is 0, 1 or 2, and $R_6$ is hydrogen, linear $C_1$–$C_6$ alkyl, branched $C_3$–$C_8$ alkyl, or $C_3$–$C_8$ alkenyl; or $R_{14}$ is $NR_{15}R_{16}$ wherein $R_{15}$ and $R_{16}$ are each independently hydrogen, linear $C_1$–$C_6$ alkyl, branched $C_3$–$C_8$ alkyl, $C_3$–$C_8$ alkenyl wherein the double bond is not adjacent to the nitrogen, or $C_3$–$C_7$ cycloalkyl-($CH_2$)$_n$ wherein n is as defined above, or $R_{15}$ and $R_{16}$ together with the nitrogen form a saturated five or six membered ring optionally condensed with benzo.

2. A compound according to claim 1 wherein Z is

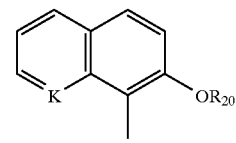

wherein K is C or N and $R_{20}$ is methyl, ethyl, isopropyl, cyclopropylmethylene, methoxyethylene or hydroxyethylene.

3. A composition for the treatment of (a) illnesses induced or facilitated by corticotropin releasing factor or (b) stress and anxiety related disorders including stress-induced depression and headache, abdominal bowel syndrome, inflammatory disorders, immune suppression, HIV infections, Alzheimer's disease, gastrointestinal diseases, anorexia nervosa, hemorrhagic stress, drug and alcohol withdrawal symtoms, drug addiction, and fertility problems, which comprises a compound of the formula I as defined in claim 1 in an amount effective in the treatment of said illnesses, and a pharmaceutically acceptable carrier.

4. A method for the treatment of (a) illnesses induced or facilitated by corticotropin releasing factor or (b) stress and anxiety related disorders including stress-induced depression and headache, abdominal bowel syndrome, inflammatory disorders, immune suppression, HIV infections, Alzheimer's disease, gastrointestinal diseases, anorexia nervosa, hemorrhagic stress, drug and alcohol withdrawal symtoms, drug addiction, and fertility problems, which comprises administering to a subject in need of such treatment a compound of formula I as defined in claim 1.

* * * * *